US 6,748,261 B1

(12) United States Patent
Kroll et al.

(10) Patent No.: US 6,748,261 B1
(45) Date of Patent: Jun. 8, 2004

(54) IMPLANTABLE CARDIAC STIMULATION DEVICE FOR AND METHOD OF MONITORING PROGRESSION OR REGRESSION OF HEART DISEASE BY MONITORING INTERCHAMBER CONDUCTION DELAYS

(75) Inventors: Mark W. Kroll, Simi Valley, CA (US); Joseph J. Florio, La Canada, CA (US); Gene A. Bornzin, Simi Valley, CA (US); Euljoon Park, Stevenson Ranch, CA (US); Kerry A. Bradley, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 550 days.

(21) Appl. No.: 09/675,462

(22) Filed: Sep. 28, 2000

Related U.S. Application Data

(60) Provisional application No. 60/202,854, filed on May 8, 2000.

(51) Int. Cl.[7] .................................................. A61B 5/04
(52) U.S. Cl. ............................ 600/510; 600/509; 607/9
(58) Field of Search ............. 607/9, 4, 14; 600/508–10, 600/515, 516

(56) References Cited

U.S. PATENT DOCUMENTS

| 5,179,949 A | 1/1993 | Chirife ........................ 128/419 |
| 5,683,426 A | * 11/1997 | Greenhut ........................ 607/9 |
| 5,720,768 A | * 2/1998 | Verboven-Nelissen ......... 607/9 |
| 5,871,511 A | 2/1999 | Bolz et al. ..................... 607/14 |
| 5,902,324 A | 5/1999 | Thompson et al. ............ 607/9 |
| 6,070,100 A | * 5/2000 | Bakels ........................... 607/9 |

OTHER PUBLICATIONS

Wilensky, Robert L., MD, et al, "Serial Electrocardiographic Changes in Idiopathic Dilated Cardiomyopathy Confirmed at Necropsy", The American Journal of Cardiology, vol. 62, pp. 276–283 (Aug. 1988).

Xiao, Han B., et al, "Effects of Abnormal Activation on the Time Course of the Left Ventricular Pressure Pulse in Dilated Cardiomyopathy", British Heart Journal, vol. 68, pp. 403–407 (1992).

Xiao, Han B., et al, "Nature of Ventricular Activation in Patients with Dilated Cardiomyopathy: Evidience for Bilateral Bundle Branch Block", British Heart Journal, vol. 72, pp. 167–174 (1994).

* cited by examiner

Primary Examiner—Angela D. Sykes
Assistant Examiner—Roderick Bradford

(57) ABSTRACT

A system and method, for use in an implantable cardiac stimulation device, monitors progression or regression in heart disease such as congestive heart failure. The system includes a sensing circuit that derives an electrogram signal indicative of the electrical activity of the patient's heart. A processor processes the electrogram signal to determine interchamber conduction delays which are then stored in memory. The stored interchamber conduction delays may be later retrieved by way of a telemetry circuit. Relative changes in the interchamber conduction delays, over time, are indicative of progression or regression in the heart disease. The relative changes in the interchamber conduction delays may be further used to automatically adjust pacing parameters of the implantable cardiac stimulation device.

57 Claims, 8 Drawing Sheets

IMPLANTABLE CARDIAC STIMULATION DEVICE FOR AND METHOD OF MONITORING PROGRESSION OR REGRESSION OF HEART DISEASE BY MONITORING INTERCHAMBER CONDUCTION DELAYS

This application claims the benefit of U.S. Provisional Application No. 60/202,854, filed May 8, 2000.

FIELD OF THE INVENTION

The present invention is generally directed to an implantable device for monitoring the progression or regression of heart disease. The present invention is more particularly directed to a system and method for use in an implantable cardiac stimulation device which determines and stores interchamber conduction delays. Relative changes in the interchamber conduction delays, over time, are indicative of the progression or regression of the heart disease.

BACKGROUND OF THE INVENTION

More people die of heart disease than any other single cause. One common form of heart disease is congestive heart failure.

Congestive heart failure (CHF) is a debilitating, disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become leaky, allowing regurgitation or backflow of blood. The impairment of arterial circulation deprives vital organs of oxygen and nutrients. Fatigue, weakness, and inability to carry out daily tasks may result.

Not all CHF patients suffer debilitating symptoms immediately. Some may live actively for years. Yet, with few exceptions, the disease is relentlessly progressive.

As CHF progresses, it tends to become increasingly difficult to manage. Even the compensatory responses it triggers in the body may themselves eventually complicate the clinical prognosis. For example, when the heart attempts to compensate for reduced cardiac output, it adds sarcomeres to the myocardial cells, causing the ventricles to grow in mass in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

Current standard treatment for heart failure is typically centered around medical treatment using ACE inhibitors, diuretics, and digitalis. It has also been demonstrated that aerobic exercise may improve exercise tolerance, improve quality of life, and decrease symptoms. Heart transplantation is an option, but only in 1 out of 200 cases. Other cardiac surgery may also be indicated, but only for a small percentage of patients with particular etiologies. Although advances in pharmacological therapy have significantly improved the survival rate and quality of life of patients, patients who are refractory to drug therapy have a poor prognosis and limited exercise tolerance. Cardiac pacing has been proposed as a new treatment for patients with drug-refractory CHF.

In patients with heart failure and atrial fibrillation (AF), the heart has often remodeled due to the disease, such that there is increased fibrosis between myocardial cells, a lengthening of the cells, varying degrees of hypertrophy and dilation, and up and down regulation of various receptors that affect ionic balance, action potential conduction, and contraction. These variations in the AF and CHF substrates often result in conduction abnormalities that may manifest in arrhythmia, which may further worsen the substrate and thus the heart's contraction synchrony.

Multi-chamber pacing (bi-ventricular or bi-atrial) has been proposed as an emerging therapy for the treatment of heart failure and atrial fibrillation. The patients who appear to gain the greatest benefit from this pacing therapy are those with the greatest dyssynchrony, since the benefit of multi-chamber pacing appears dependent upon chamber synchronization and/or appropriate sequencing.

It is desirable to have a system which would track the progression or regression of the patient's disease, particularly as it relates to the success of any therapy in halting or reversing the remodeling. A good metric of the heart's reverse remodeling is the degree to which the myocardium conducts the depolarization wave, since this relates directly to chamber synchrony.

The hemodynamic consequences of abnormal ventricular activation in dilated cardiomyopathy patients have been extensively studied. These studies account for the presence of major delay and nonuniformity in left ventricular (LV) contraction and relaxation in patients with poor LV function and high-degree interventricular conduction block. Hence, the degree of interventricular conduction delay may be used as a surrogate measurement for the disease state of heart. Additionally, patients prone to atrial fibrillation are likely to have a long interatrial conduction delay. Restoration of atrial chamber synchrony/sequencing may be critical in reducing the incidence of AF in these patients.

By tracking the progression or regression of heart disease, such as CHF, more closely, treatments could be managed more effectively. Commonly, patients with heart disease have an implanted cardiac stimulation device. Hence, it would be advantageous if the implanted cardiac stimulation device were able to aid in the tracking of the progression or regression of the heart disease. The present invention provides a system and method for use in such a device capable of tracking heart disease progression or regression by measuring interchamber conduction delays over time.

SUMMARY OF THE INVENTION

The present invention provides a system and method, for use in an implantable cardiac stimulation device, for monitoring progression or regression in heart disease such as congestive heart failure. A sensing circuit produces an electrogram signal indicative of the electrical activity of the patient's heart. A processor processes the electrogram signal to determine interchamber conduction delays which are then stored in memory. The stored interchamber conduction delays may be retrieved by way of a telemetry circuit. Relative changes in the interchamber conduction delays, over time, are indicative of progression or regression in the heart disease.

The determined interchamber conduction delays may be the times between activations of corresponding ventricular or atrial chambers of the heart. The interchamber delays may alternatively be the times between the delivery of a pacing pulse to one chamber and the intrinsic depolarization of its corresponding chamber. The interchamber conduction delays may alternatively be the average of the right chamber to left chamber conduction delay and the left chamber to right chamber conduction delay.

The relative changes in the interchamber conduction delays may be further used for automatic pacing parameter adjustment. If the relative changes in the interchamber conduction delays indicate a decreasing trend, pacing rate may be decreased or AV delay may be increased to allow the patient's heart to function more on its own without pacing intervention.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
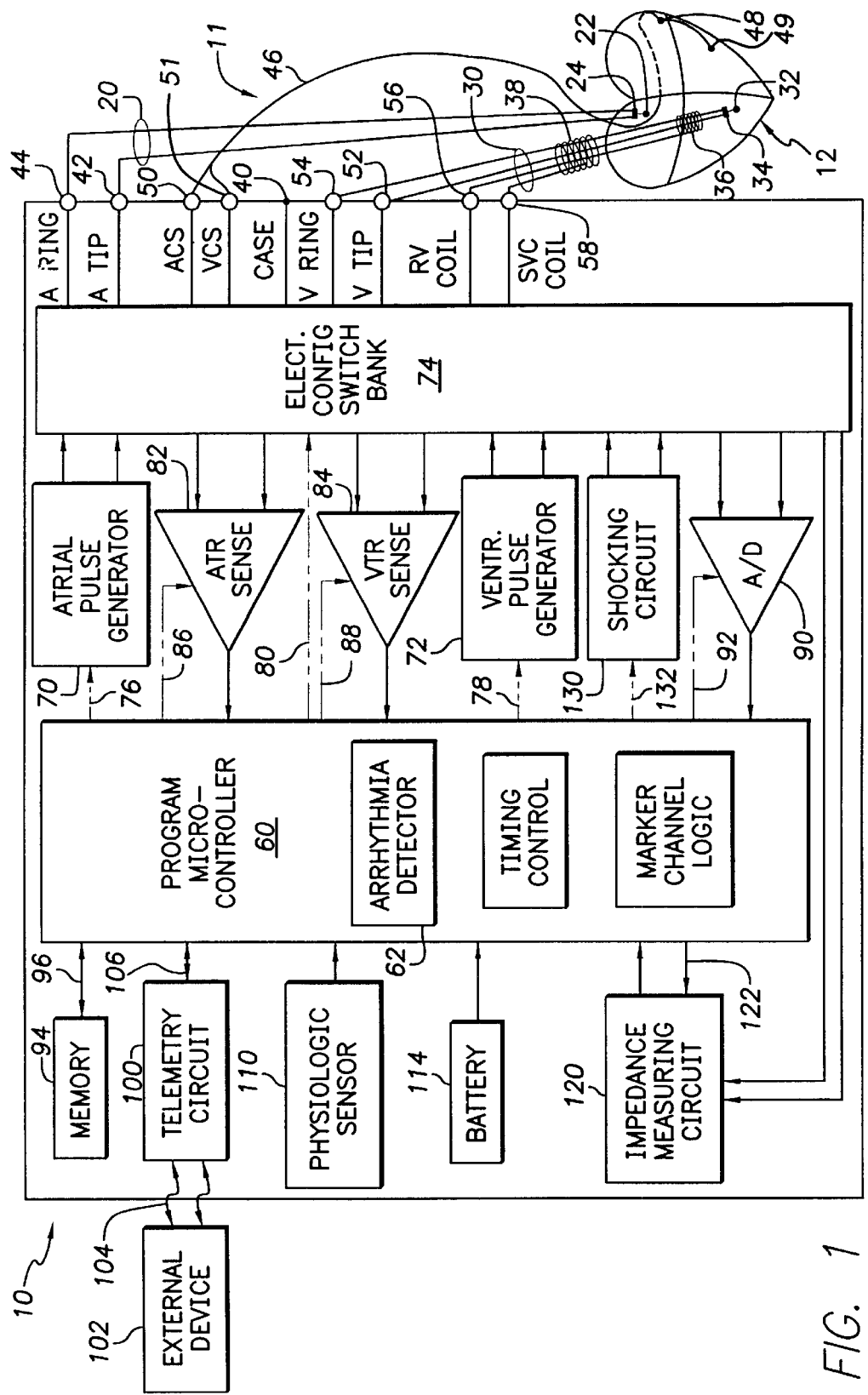
FIG. 1 is a functional block diagram of a dual-chamber implantable stimulation device illustrating the basic elements of a stimulation device which can provide cardioversion, defibrillation and pacing stimulation.

In FIG. 1, a simplified block diagram is shown of a dual-chamber, multi-site implantable stimulation device 10 which embodies the present invention and is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's right atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular chamber and the SVC coil electrode 38 in the superior vena cava. Accordingly, the ventricular lead 30 is capable of receiving cardiac signals and delivering stimulation in the form of pacing and shock therapy to the right ventricle.

Further, in accordance with this preferred embodiment, the lead system includes a coronary sinus (CS) lead 46 having a left atrial pacing and sensing electrode 48 and a left ventricular pacing and sensing electrode 44. The CS lead 46 may be advanced through the SVC, into the right atrium, through the ostium of the coronary sinus and into the coronary sinus for placing the electrode 48 adjacent the left atrium and the electrode 49 adjacent the left ventricle. With the lead 46 thus positioned, it is capable of providing pacing stimulation to the left side of the heart, either the left atrium or left ventricle, or both. Further, electrode 48 may provide bi-atrial pacing with electrode 22, and electrode 49 may provide bi-ventricular pacing with electrode 32. Further, electrodes 32 and 49 may also be used to generate an electrogram signal from which the interchamber conduction delays may be determined.

The housing 40 (shown schematically) for the stimulation device 10 includes a connector (not shown) having an atrial tip terminal 42 and an atrial ring terminal 44, which are adapted for connection to the atrial tip electrode 22 and the atrial ring electrode 24, respectively. The housing 40 further includes a ventricular tip terminal 52, a ventricular ring terminal 54, a right ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 still further includes an atrial coronary sinus (CS) terminal 50 and a ventricular CS terminal 51 adapted for connection to the atrial CS electrode 48 and ventricular CS electrode 49, respectively. The housing 40 (often referred to as the "can", "case" or "case electrode") may be programmably selected to act as the return electrode, or anode, alone or in combination with one of the coil electrodes, 36 and 38, ventricular pacing electrodes 32 and 49, or atrial pacing electrodes, 22 and 48. For convenience, the names of the electrodes are shown next to the terminals.

The stimulation device 10 further includes a programmable microcontroller 60 which controls the various modes of stimulation therapy. As is well known in the art, the microcontroller 60 includes a microprocessor, or equivalent control circuitry or processor, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

As shown in FIG. 1, an atrial pulse generator 70 and a ventricular pulse generator 72 generate pacing stimulation pulses for delivery to the right atrium through lead 20, the right ventricle through lead 30, and the left atrium and left ventricle through lead 46 via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the operation of the stimulation device timing of such stimulation pulses, e.g., pacing rate and atrio-ventricular (AV) delay, as well as keeping track of the timing of any refractory periods, PVARP intervals, noise detection windows, evoked response windows, alert intervals, marker channel timing, etc., that are well known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the type of stimulation therapy (e.g., unipolar, bipolar, or multi-chamber) by selectively closing the appropriate combination of switches (not shown) as is known in the art.

An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control can enable the device 10 to deal effectively with the difficult problem of sensing the low frequency, low amplitude signal characteristics of ventricular fibrillation.

The outputs of the atrial and ventricular sense amplifiers, 82 and 84, are connected to the microcontroller 60 which, in turn, inhibit the atrial and ventricular pulse generators, 70 and 72, respectively, in a demand fashion whenever cardiac activity is sensed in the respective chambers. The sense amplifiers, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sense amplifiers, 82 and 84, as is known in the art.

For arrhythmia detection, the device 10 utilizes the atrial and ventricular sense amplifiers, 82 and 84, to sense cardiac signals to determine whether a rhythm is physiologic or pathologic. As used herein "sensing" is reserved for the noting of an electrical depolarization and "detection" is the processing of these sensed depolarization signals and noting the presence of an arrhythmia. The timing intervals between sensed events (e.g., the P—P and R—R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks); the scheduling of these therapies is known as "tiered therapy").

Cardiac signals are also applied to the inputs of an analog to digital (A/D) data acquisition system 90. The data acquisition system 90 is configured to sense or acquire intracardiac electrogram signals, convert the raw analog data into a digital signal, and store the digital signals for later processing and/or telemetric transmission to an external device 102. The data acquisition system 90 is preferably coupled to the ventricular electrodes 49 and 32 of leads 46 and 30, respectively, through the switch bank 74 to sample cardiac signals from both sides of the heart 12 to generate an electrogram signal representing electrical activity of the heart from which the interchamber conduction delays may be determined. The data acquisition system 90 is coupled to the microcontroller for detecting activations and evoked responses of the heart for measuring the interchamber conduction delays.

The microcontroller 60 is further coupled to a memory 94 by a suitable data/address bus 96, where the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 28 within each respective tier of therapy. The memory 94 further serves to store the interchamber conduction delays. In accordance with the present invention, the microcontroller 60 may use the stored interchamber conduction delays to adjust the pacing parameters of the stimulation device 10.

Advantageously, the operating parameters of the implantable stimulation device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms, status information relating to the operation of the device 10, and the stored interchamber conduction delays (as contained in the microcontroller 60 or memory 94), and heart disease monitoring results to be sent to the external device 102 through an established communication link 104 for analysis.

In the preferred embodiment, the stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV delay at which the atrial and ventricular pulse generators, 70 and 72, generate stimulation pulses. The type of sensor used is not critical to the present invention and is shown only for completeness.

The stimulation device additionally includes a battery 114 which provides operating power to all of the circuits shown in FIG. 1. For the stimulation device 10, which employs shocking therapy, the battery must be capable of operating at low current drains for long periods of time, and then be capable of providing high-current pulses (for capacitor charging) when the patient requires a shock pulse. The battery 114 must also have a predictable discharge characteristic so that elective replacement time can be detected. Accordingly, the device 10 employs lithium/silver vanadium oxide batteries, as is currently true for many such devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 1, the device 10 preferably also includes an impedance measuring circuit 120 which is enabled by the microcontroller 60 by a control signal 122. The known uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 120 is advantageously coupled to the switch bank 74 so that it may be coupled to any desired electrode (including the RV and SVC coil electrodes, 36 and 38). The impedance measuring circuit 120 is not critical to the present invention and is shown only for completeness.

The device 10 is further capable to function as an implantable cardioverter/defibrillator (ICD) device. That is, it may detect the occurrence of an arrhythmia, and automatically apply an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 joules), moderate (0.5–10 joules), or high energy (11–40 joules), as controlled by the microcontroller 60. Such shocking pulses are applied to the patient's heart through at least two shocking electrodes, as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (e.g., using the RV electrode 36 as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 2:
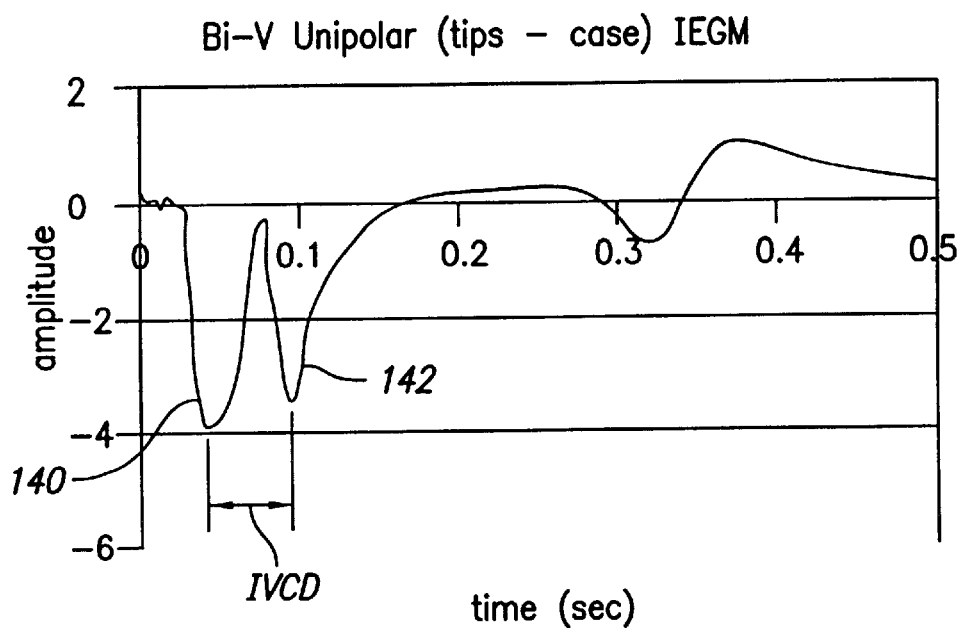
FIG. 2 illustrates an electrogram signal which may be generated in accordance with the present invention and one method of determining an interchamber conduction delay embodying the present invention.

FIG. 2 illustrates an IEGM generated by the data acquisition system 90 which the microcontroller 60 (FIG. 1) may use to determine an interchamber conduction delay. As may be seen in FIG. 2, two ventricular activations 140 and 142 are displayed. The activations may both be intrinsic activations or one activation, for example activation 140, may be an evoked response to a pacing pulse while the other activation, for example activation 142, may be the resulting intrinsic activation from the activation wave initiated by the evoked response. Activation 140 is the activation of the right ventricle and activation 142 is the activation of the left ventricle. The interchamber conduction delay, here an interventricular conduction delay (IVCD), is the time between the activations and more particularly, the time between the activation peaks. Methods, such as detection of changing slope signs, as are known in the art, may be employed for locating the activation peaks to determine the time between the peaks.

The activations, as previously mentioned, may both be intrinsic activations. In this event, pacing is not required to determine the interchamber conduction delay. However, for those patients lacking in intrinsic heart activity, the interchamber conduction delay may be determined by applying a pacing pulse to one chamber, such as the right ventricle, and measuring the time between the right ventricular evoked response and the left ventricular activation resulting from the right ventricular evoked response.

The process may also be carried out in the other direction. Here, the left ventricle would be paced and the interchamber conduction delay determined between the time of the left ventricular evoked response and the time of the resulting right ventricular activation.

The pacing pulses may be delivered by selectively utilizing a bipolar electrode pair or unipolar electrode and the device case. However, multi-chamber pacing has been found to be advantageous for some patients. Here, a pacing pulse is simultaneously applied to both right and left corresponding chambers. This may be done with two unipolar electrodes, such as electrodes 32 and 49 (FIG. 1) while using the device case 40 as a common return electrode. As is known in the art, pacing stimulation thresholds are generally lower when endocardially pacing the right side of the heart than when epicardially pacing the left side of the heart. Hence, when a pacing system is configured for multi-chamber pacing, selective stimulation of the right side of the heart may be accomplished by selecting a stimulation pulse energy that is above the stimulation threshold of the right side of the heart, but below the stimulation threshold of the left side of the heart. The result is an evoked response of the right heart side chamber and an intrinsic activation of the corresponding left heart side chamber.

Figure 3:
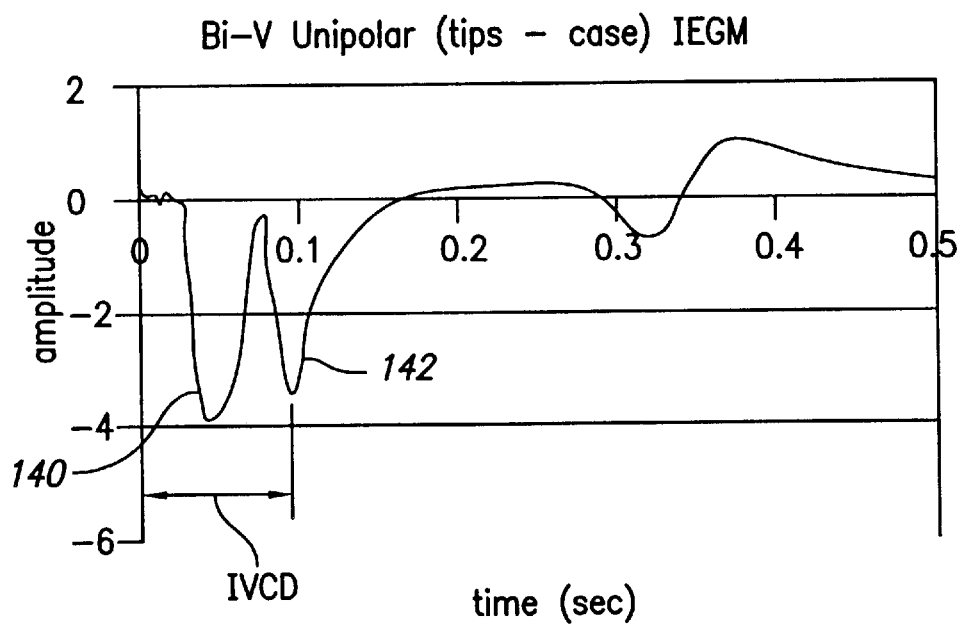
FIG. 3 illustrates the electrogram signal of FIG. 2 and another method of determining an interconduction delay embodying the present invention.

FIG. 3 illustrates a different method of determining interchamber conduction delay using the same IEGM depicted in FIG. 2. Here, the interchamber conduction delay is measured by determining the time between the time of providing the pacing stimulus (T=0) to one chamber and the time of the resulting activation of the corresponding chamber. Hence, as illustrated in FIG. 3, the interventricular conduction delay (IVCD) is the time between the provision of the pacing pulse, either solely to the right ventricle or simultaneously to both the right and left ventricles with an energy above the right ventricle threshold and below the left ventricle threshold, to the activation 142 of the left ventricle.

The foregoing discussion, of course, is equally as applicable to determining inter-atrial conduction delays. The inter-atrial conduction delays may be determined from intrinsic activations of both atria or the provision of a pacing stimulus to one atrium and then noting the time of the resulting activation of the other atrium. As with the ventricular pacing as discussed above, the atrial pacing may be selective or bi-atrial.

FIGS. 4–6 are flow charts describing different methods of operation that the microcontroller 60 (FIG. 1) may execute in determining interchamber conduction delays over time and automatically adjusting pacing parameters responsive to the interchamber conduction delays in accordance with the present invention. In these flow charts, the various algorithmic steps are summarized in "blocks". Such blocks describe specific actions or decisions that are carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Figure 4A:
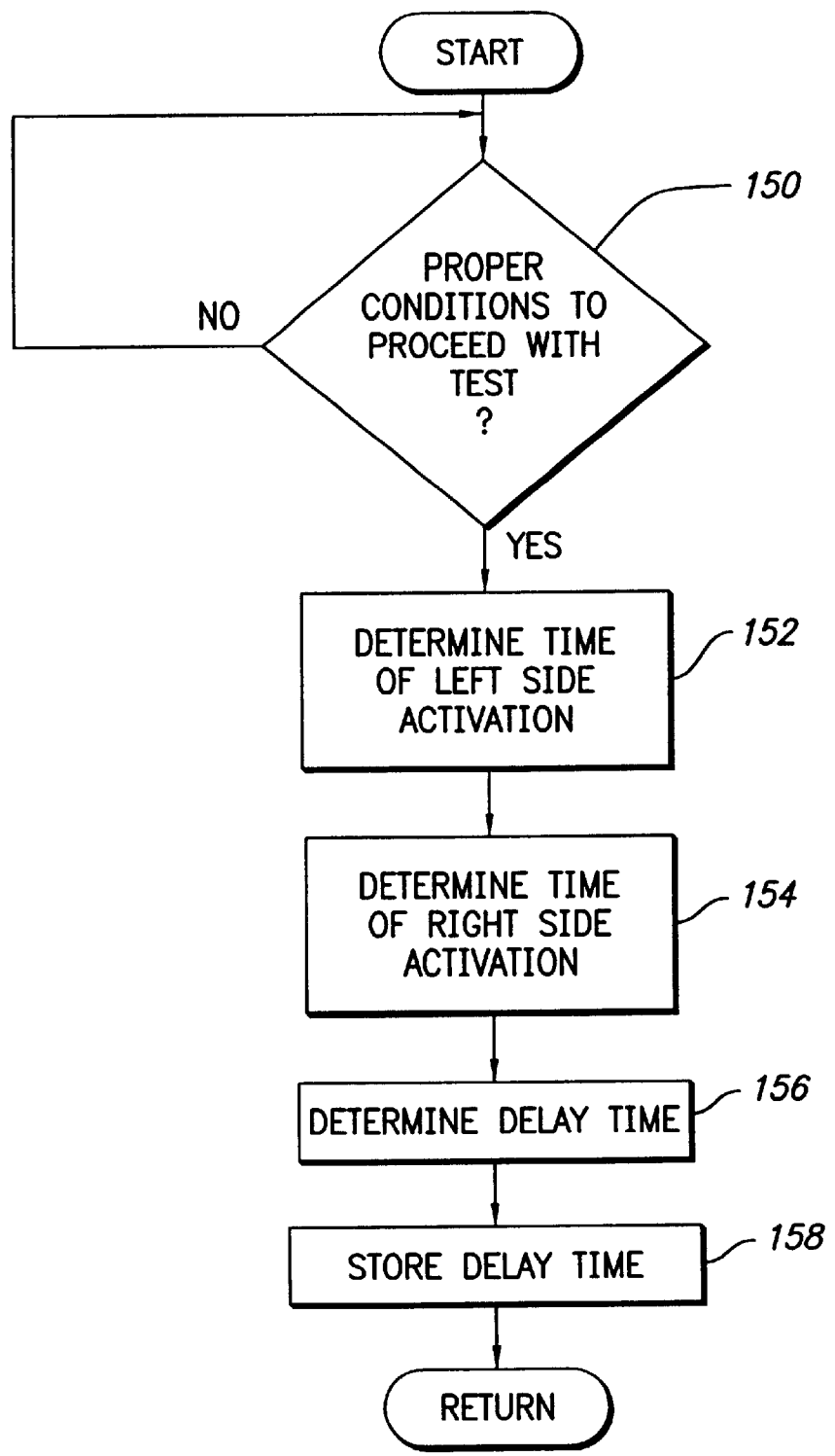
FIGS. 4A and 4B are flow charts describing one embodiment of monitoring the progression or regression of a patient's heart disease in accordance with the present invention.

FIG. 4A is a flow chart illustrating a method for determining interchamber conduction delays from intrinsic heart activity. In this flow chart and the other flow charts of FIGS. 5 and 6, "right side" is meant to denote the right ventricle or right atrium and "left side" is meant to denote the corresponding left ventricle or left atrium.

The process initiates at a decision block 150 where it is determined whether proper conditions exist to measure an interchamber conduction delay. The interchamber conduction delays may be determined at periodic intervals as, for example, a predetermined number of times per day, or subject to other test conditions, e.g., heart rate or patient activity level. If proper conditions exist to measure an interchamber conduction delay, the last cardiac cycle of the IEGM produced by the data acquisition system 90 and stored in memory 94 is utilized. The process then advances to an activity block 152 where the time of the left side activation is determined. As previously described, the peak of the left side activation may be utilized for this purpose and detected by slope sign change detection or other methods known in the art. After the time of the left side activation is determined, the process then advances to an activity block 154 where the time of the right side activation is determined. Again, the time of the right side activation may be taken as the peak of the right side activation.

After the time of the right side activation is determined in accordance with activity block 154, the process advances to activity block 156 where the interchamber conduction delay is determined. More specifically, as discussed with respect to FIG. 2, the interchamber conduction delay may be determined by measuring the time between the peak of the right side activation and the peak of the left side activation. Once the interchamber conduction delay is determined in accordance with activity block 156, the process advances to activity block 158 where the interchamber conduction delay just determined is stored in the memory 94. The interchamber conduction delay just determined is now available for later retrieval by the external device 102 by way of the telemetry circuit 100.

Figure 4B:
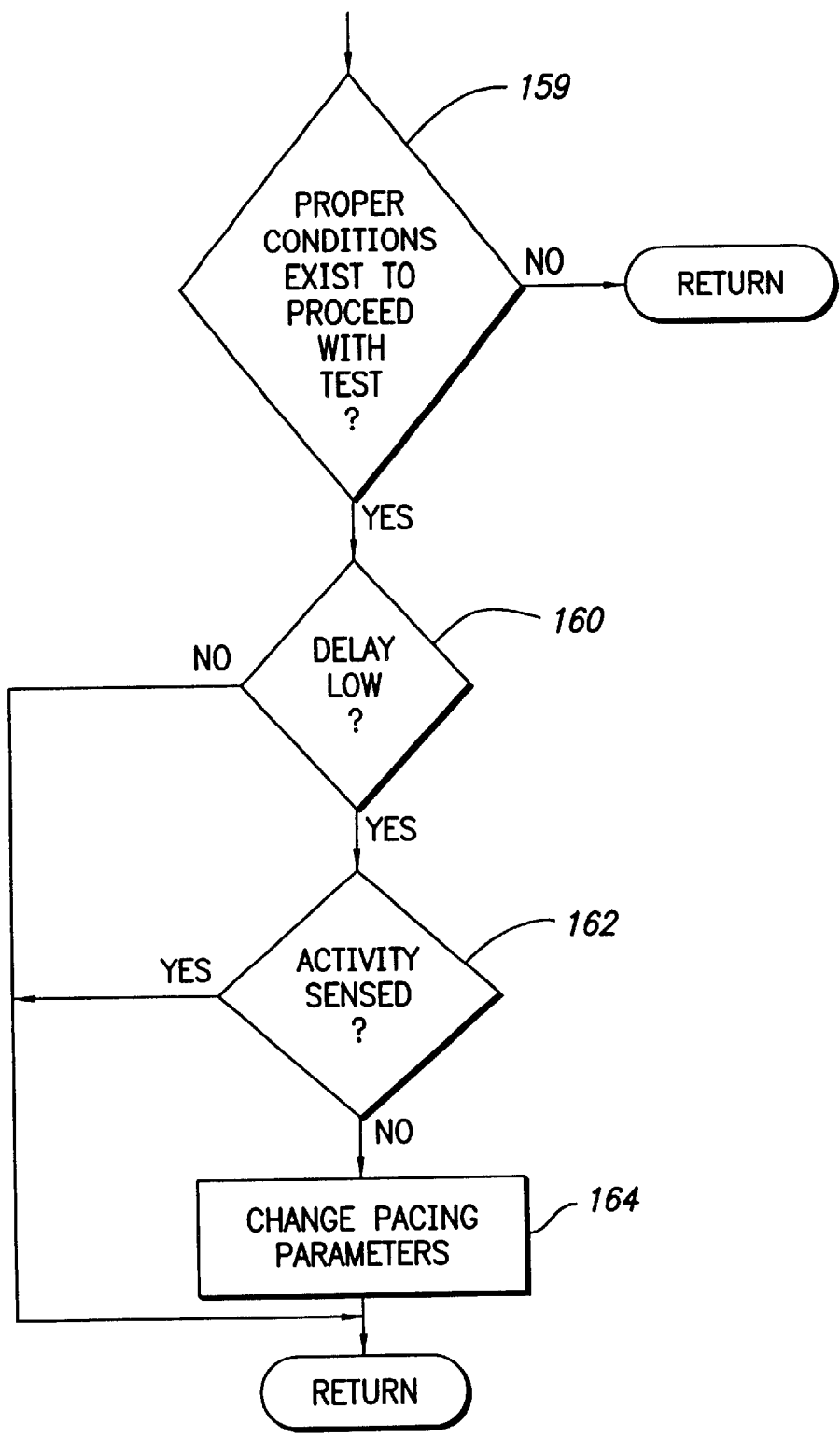

In bock 159 of FIG. 4B, it is subsequently determined whether the data stored in block 158 should be processed. This test may occur directly following the processing in block 158. Alternatively, this test may occur periodically at predetermined times, e.g., at a lower rate than the data is stored in block 158. If this criteria has been satisfied, the process then advances to decision block 160 which determines if the interchamber conduction delay is lower than a predetermined delay time. If the interchamber conduction delay time is not below the predetermined delay time, the process returns. However, if it is, reverse remodeling of the heart may be indicated which may in turn indicate the desirability of adjusting pacing parameters. Hence, the process then advances to decision block 162 where it is determined if intrinsic activity of the heart is being sensed at frequent intervals. Decision block 162 may be carried out by noting the percentage of cardiac cycles which have been paced over a predetermined number of cardiac cycles. If the percentage of cardiac cycles being paced is higher than would be indicated by the interchamber conduction delay, the process then advances to an activity block 164 where the pacing parameters are changed. The change in pacing parameters may include a decrease in pacing rate or a lengthening in the AV delay to permit the patient's heart to function intrinsically more often without pacing intervention. The process then returns.

If, when performing decision block 162 it is determined that the percentage of cardiac cycles being paced is commensurate with the interchamber conduction delay, a change in pacing parameters will not be indicated. As a result, the process will immediately return from decision block 162.

Figure 5A:
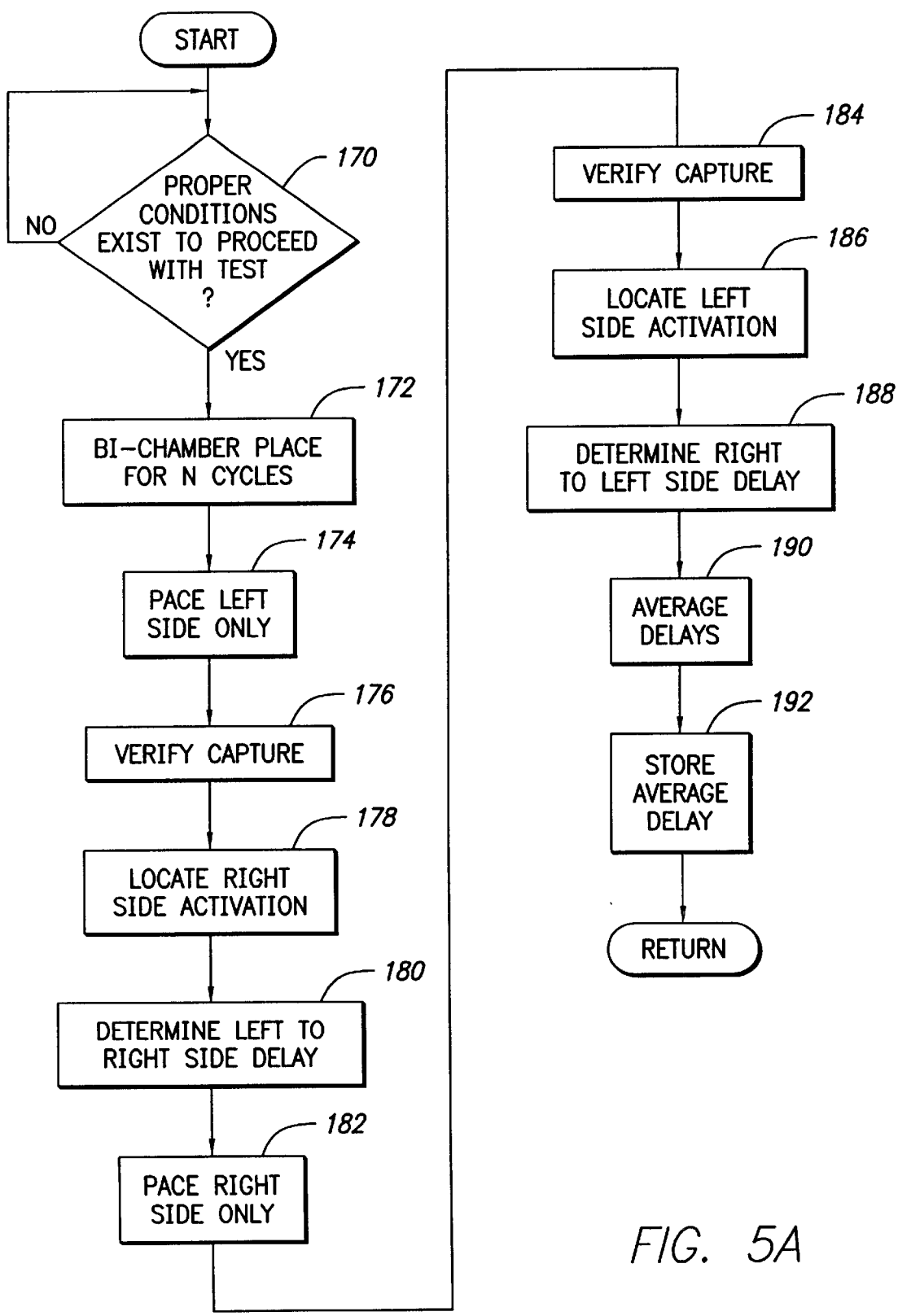
FIGS. 5A and 5B are flow charts describing another embodiment of the present invention.

FIG. 5A is a flow diagram illustrating another embodiment for determining interchamber conduction delays in accordance with the present invention. Here, the interchamber conduction delays are determined by first selectively pacing the left side of the heart and measuring the interconduction delay to the resulting activation of the right side of the heart, selectively pacing the right side of the heart and measuring the interchamber conduction delay to the resulting activation of the left side of the heart, and then averaging the interchamber conduction delays.

The process initiates at decision block 170 where it is determined if proper conditions exist (in a manner similar to that described in reference to block 150 of FIG. 4A) to measure the interchamber conduction delay. If the proper conditions exist, the system first conditions the heart for the interchamber conduction delay measurement by multichamber pacing and capturing both paced chambers of the heart for a predetermined number (N) of cycles, e.g., 10 cycles, in activity block 172. When activity block 172 is completed, the process then advances to activity block 174 where the left side of the heart is selectively paced. Activity block 174 may be carried out by utilizing a bipolar electrode pair in the coronary sinus adjacent the selected left side heart chamber or by utilizing a unipolar electrode in the coronary sinus adjacent the selected left heart side chamber and the device case as a return electrode. Once the left side of the heart is paced, the capture of the left side of the heart is verified in activity block 176. As is known in the art, capture occurs when an electrical stimulus applied to the heart is of sufficient energy to depolarize the cardiac tissue, thereby causing the heart muscle to contract. The microcontroller 60 (FIG. 1) detects a depolarization signal during a window following a stimulation pulse, the presence of which indicates that capture has occurred.

Once capture is verified in accordance with activity block 176, the process then continues to activity block 178 where the resulting activation of the corresponding heart right side chamber is located. Upon completion of activity block 178, the process then advances to activity block 180 where the interchamber conduction delay from the left side of the heart to the right side of the heart is determined and temporarily stored.

After the interchamber conduction delay from the left side of the heart to the right side of the heart is determined in accordance with activity block 180, the process advances to activity block 182 where the right side of the heart is selectively paced. Following the pacing of the right side of the heart, capture of the right side of the heart is verified in activity block 184. Next, the resulting activation of the corresponding heart left side chamber is located in activity block 186. After the resulting activation of the corresponding left heart side chamber is determined in accordance with activity block 186, the process then advances to activity block 188 where the interchamber conduction delay from the right side of the heart to the left side of the heart is determined. The final interchamber conduction delay is then determined in accordance with activity block 190 by averaging the interchamber conduction delays determined in activity blocks 180 and 188. The final interchamber conduction delay is then stored in the memory 94 in accordance with activity block 192. Optionally, the left to right and right to left interchamber conduction delays may be determined and stored separately in memory 94.

The interchamber conduction delays determined in activity blocks 180 and 188 may be determined as illustrated in either FIG. 2 or FIG. 3. The interchamber conduction delays hence may be determined, by measuring the time between the evoked response of the paced chamber and the resulting activation of the corresponding unpaced chamber. Alternatively, the interchamber conduction delays may be determined by measuring the time between the provision of the pacing stimulus to the activation of the unpaced chamber.

Figure 5B:
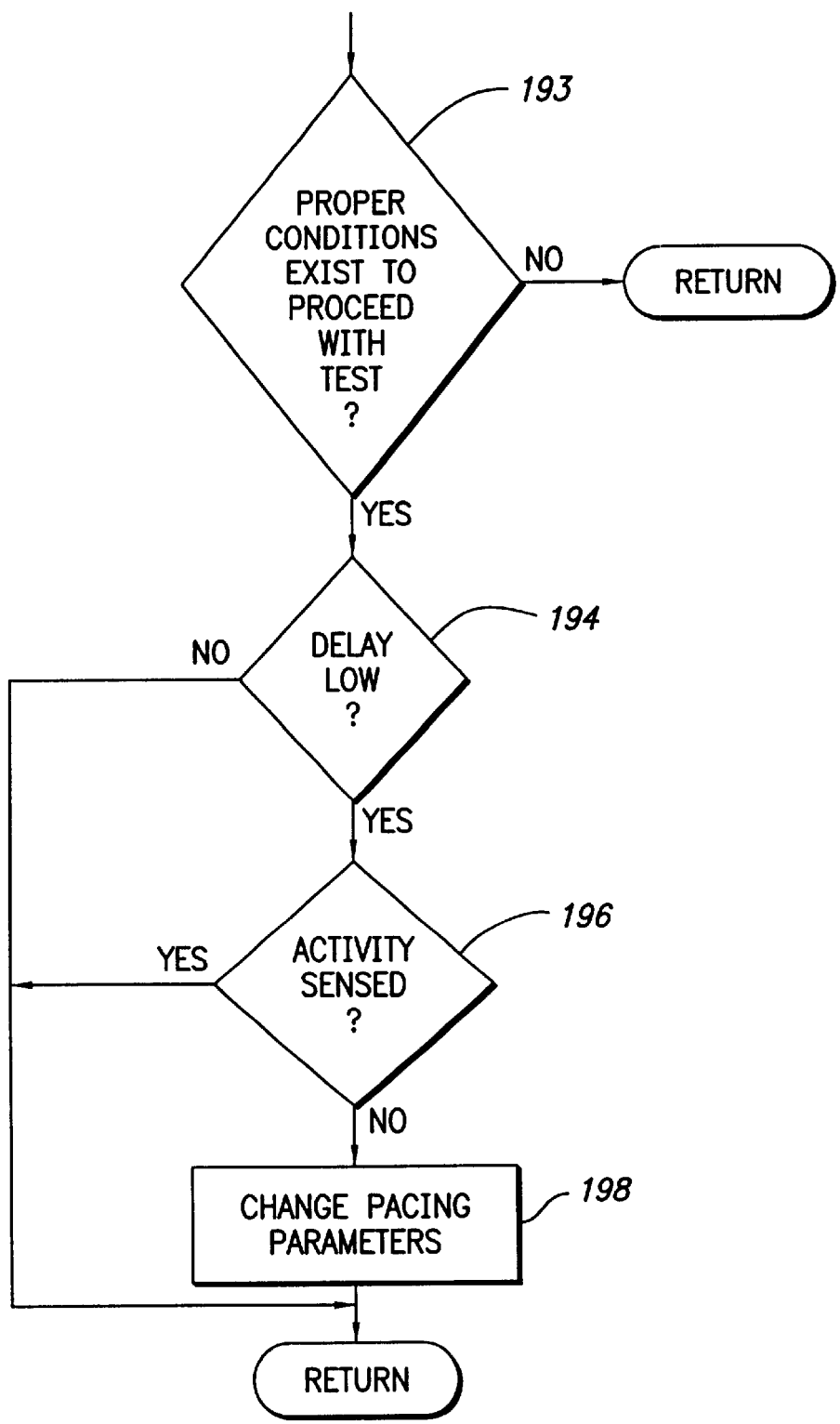

In bock 193 of FIG. 5B, it is subsequently determined whether the data stored in block 192 should be processed. This determination is done in a similar manner to that previously described in reference to block 159 of FIG. 4B. If the criteria of block 193 has been satisfied, the process advances to decision block 194 which determines if the interchamber conduction delay is lower than the predetermined delay time. If the interchamber conduction delay time is not below the predetermined delay time, the process returns. However, if it is, reverse remodeling of the heart may be indicated which may in turn indicate the desirability of adjusting pacing parameters. Hence, the process then advances to decision block 196 where it is determined if intrinsic activity of the heart is being sensed at frequent enough intervals. Decision block 196 may be performed by noting the percentage of cardiac cycles which have been paced over a predetermined number of cardiac cycles. If the percentage of paced cardiac cycles is higher than would be indicated by the interchamber conduction delay, the process then advances to activity block 198 where the pacing parameters are changed. Again, the change in pacing parameters may include a decrease in pacing rate or a lengthening in the AV delay to permit the patient's heart to function intrinsically more often without pacing intervention. The process then returns.

If when performing decision block 196 it is determined that the percentage of paced cardiac cycles is commensurate with the measured interchamber conduction delay, a change in pacing parameters will not be indicated. As a result, the process will immediately return.

Figure 6A:
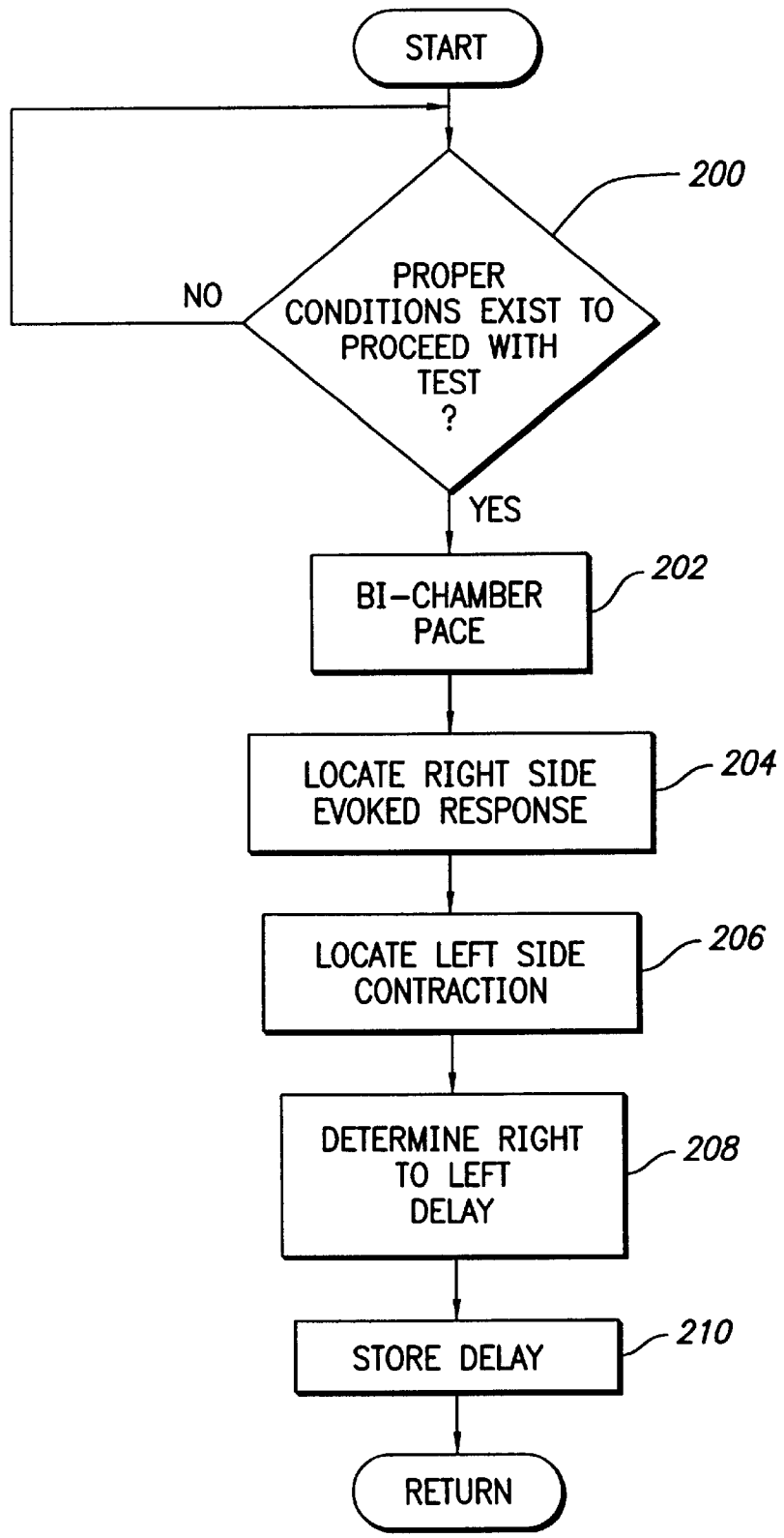
FIGS. 6A and 6B are flow charts describing still another embodiment of the present invention.

FIG. 6A is a flow chart illustrating another method of determining interchamber conduction delays in accordance with the present invention. As will be seen hereinafter, the process described by the flow chart of FIG. 6 includes multi-chamber pacing by simultaneously applying pacing pulses to the right and left sides of the heart, where the pacing pulses have an energy above the stimulation threshold of the right side of the heart but below the stimulation threshold of the left side of the heart. This produces an evoked response of the right heart side chamber and a resulting intrinsic depolarization of the corresponding left heart side chamber.

The process of FIG. 6A initiates with decision block 200 where it is determined if proper conditions exist (in a manner similar to that described in reference to block 150 of FIG. 4A) to measure the interchamber conduction delay. If the proper conditions exist, the process advances to activity block 202 where the heart is multi-chamber paced. After the cardiac cycle is completed which includes the multi-chamber pacing pulses of activity block 202, the IEGM is utilized to locate the evoked response of the right side chamber of the heart in activity block 204. After the evoked response of the right heart side chamber is located, the process advances to activity block 206 where the resulting contraction of the corresponding left heart side chamber is located. Following activity block 206, the process advances to activity block 208 where the interchamber conduction delay is determined. Although it is contemplated in accordance with this embodiment that the interchamber conduction delay be determined by measuring the time between the right ventricular evoked response and the resulting left ventricular activation, activity block 208 may alternatively be accomplished by measuring the time between the provision of the simultaneous pacing pulses and the resulting intrinsic activation of the left heart side chamber.

Following activity block 208, the interchamber conduction delay is stored in the memory 94 in accordance with activity block 210. The interchamber conduction delay is now available in memory 94 for later retrieval.

Figure 6B:
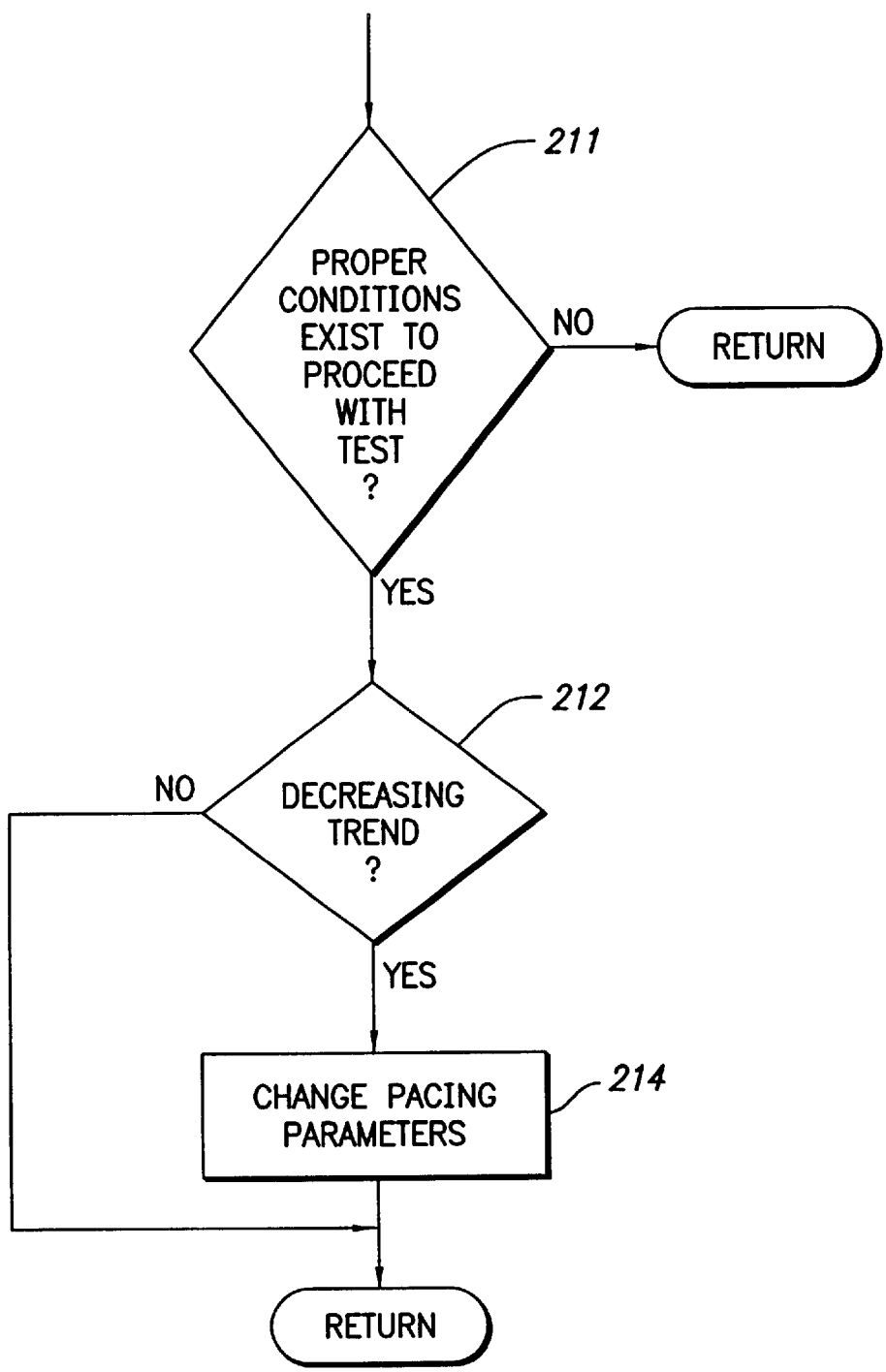

In bock 211 of FIG. 6B, it is subsequently determined whether the data stored in block 210 should be processed. This determination is done in a similar manner to that previously described in reference to block 159 of FIG. 4B. If the criteria of block 211 has been satisfied, the process advances to decision block 212 where it is determined if there is a decreasing trend in the interchamber conduction delay. Decision block 212 may be accomplished by comparing a predetermined number of the last interchamber conduction delays determined. If there is not a decreasing trend in the interchamber conduction delays, the process returns. However, if there is a decreasing trend in the interchamber conduction delays indicating a reverse remodeling of the heart, the process then advances to activity block 214 where the pacing parameters are adjusted. By virtue of a decreasing trend in the interchamber conduction delays, the pacing parameters may be adjusted by decreasing the pacing rate or increasing the AV delay towards allowing the patient's heart to function more on its own without pacemaker intervention. Following activity block 214, the process returns.

As can thus be seen from the foregoing, the present invention provides a system and method for use in an implantable cardiac device for monitoring progression or regression in heart disease such as congestive heart failure. The monitoring of the heart disease in accordance with the present invention makes use of existing circuitry commonly available in implantable cardiac stimulation devices. The interchamber conduction delays determined over time provide an indication of the progression or regression of the heart disease. This permits the physician, upon retrieval of the determined interchamber conduction delays, to alter therapy for the patient. In addition, automatic adjustment of the pacing parameters is made available in response to the interchamber conduction delays.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. In an implantable cardiac stimulation device, a system that monitors progression or regression of a patients heart disease, the system comprising:

a sensor that senses electrical activity of the patient's heart;

a processor, coupled to the sensor and configured to determine data indicative of interchamber conduction delays of the patient's heart, wherein the processor monitors the progression or regression of the heart disease by determining relative changes in the interchamber conduction delays over time; and a memory that stores the determined data.

2. The system of claim 1 further including a telemetry circuit that is configured to convey the stored data to an external device.

3. The system of claim 1 wherein the sensors monitor the times between activations of corresponding chambers of the heart to determine the interchamber conduction delays and wherein the processor is configured to determine the times between activations of the corresponding chambers.

4. The system of claim 3 wherein the corresponding chambers are the right ventricle and the left ventricle.

5. The system of claim 3 wherein the corresponding chambers are the right atrium and the left atrium.

6. The system of claim 1 further including a pulse generator configured to deliver pacing pulses to a chamber of the heart and wherein the processor is configured to determine the interchamber conduction delays as the times between deliverances of pacing pulses to the chamber of the heart and resulting intrinsic contractions of a corresponding chamber of the heart.

7. The system of claim 1 further including a pulse generator configured to deliver pacing pulses to a chamber of the heart and wherein the processor is programmed to determine the interchamber conduction delays as the times between evoked responses of the chamber and the resulting intrinsic contractions of the corresponding chamber.

8. The system of claim 7 wherein the chamber and the corresponding chamber are the right ventricle and the left ventricle.

9. The system of claim 7 wherein the chamber and the corresponding chamber are the right atrium and the left atrium.

10. The system of claim 1 further including a pulse generator configured to deliver simultaneous multi-chamber pacing pulses to corresponding first and second chambers of the patient's heart, the multi-chamber pacing pulses having energies suitable to cause evoked responses of only the first chamber and result in intrinsic contractions of the second chamber, and wherein the processor is configured to determine the interchamber conduction delays as the times between deliverances of the simultaneous multi-chamber pacing pulses and resulting intrinsic contractions of the second chamber of the heart.

11. The system of claim 6 wherein the chamber and the corresponding chamber are the right ventricle and the left ventricle.

12. The system of claim 6 wherein the chamber and the corresponding chamber are the right atrium and the left atrium.

13. The system of claim 10 wherein the corresponding chambers are the ventricles of the heart.

14. The system of claim 10 wherein the corresponding chambers are the atria of the heart.

15. The system of claim 1 further including a pulse generator configured to deliver simultaneous multi-chamber pacing pulses to corresponding first and second chambers of the patient's heart, the multi-chamber pacing pulses having energies suitable to cause evoked responses of the first chamber and result in intrinsic contractions of the second chamber; and wherein
   the processor is programmed to determine the interchamber conduction delays as the times between evoked responses of the first chamber and resulting intrinsic contractions of the second chamber of the heart.

16. The system of claim 15 wherein the corresponding chambers are the ventricles of the heart.

17. The system of claim 15 wherein the corresponding chambers are the atria of the heart.

18. The system of claim 1 wherein the implantable cardiac stimulation device includes a pulse generator configured to deliver pacing pulses to the heart, wherein programmed pacing parameters determine the pacing pulses; and wherein
   the processor is configured to revise the pacing parameters in response to the relative changes in the determined interchamber conduction delays.

19. In an implantable cardiac stimulation device, a system for monitoring progression or regression of a patient's heart disease, the system comprising:
   sensing means for sensing a heart activity signal representing electrical activity of the patient's heart;
   detecting means for detecting cardiac events in the heart activity signal;
   determining means responsive to the detecting means for determining interchamber conduction delays of the heart, wherein the determining means monitors the progression or regression of the heart disease by determining relative changes in the interchamber conduction delays over time; and
   memory means for storing the interchamber conduction delays for later analysis.

20. The system of claim 19 further including telemetry means for conveying the stored interchamber conduction delays to an external receiver.

21. The system of claim 19 wherein sensing means monitors the times between activations of corresponding chambers of the heart to determine the interchamber conduction delays and wherein the determining means include means for determining the times between activations of the corresponding chambers.

22. The system of claim 21 wherein the corresponding chambers are the right ventricle and the left ventricle.

23. The system of claim 21 wherein the corresponding chambers are the right atrium and the left atrium.

24. The system of claim 19 further including pulse generator means for delivering pacing pulses to a chamber of the heart and wherein the determining means includes means for determining the interchamber conduction delays as the times between deliverances of pacing pulses to the chamber of the heart and resulting intrinsic contractions of a corresponding chamber of the heart.

25. The system of claim 19 further including pulse generator means for delivering pacing pulses to a chamber of the heart and wherein the determining means include means for determining the interchamber conduction delays as the times between evoked responses of the chamber and the resulting intrinsic contractions of the corresponding chamber.

26. The system of claim 25 where the chamber and the corresponding chamber are the right ventricle and the left ventricle.

27. The system of claim 25 wherein the chamber and the corresponding chamber are the right atrium and the left atrium.

28. The system of claim 19 further including pulse generator means for delivering simultaneous multi-chamber pacing pulses to corresponding first and second chambers of the patient's heart, the multi-chamber pacing pulses having energies suitable to cause evoked responses of only the first chamber and result in intrinsic contractions of the second chamber; and wherein
   the determining means include means for determining the interchamber conduction delays as the times between evoked responses of the first chamber and resulting intrinsic contractions of the second chamber of the heart.

29. The system of claim 24 wherein the chamber and the corresponding chamber are the right ventricle and the left ventricle.

30. The system of claim 24 wherein the chamber and the corresponding chamber are the right atrium and the left atrium.

31. The system of claim 19 further including pulse generator means for delivering simultaneous multi-chamber pacing pulses to corresponding first and second chambers of the patient's heart, the multi-chamber pacing pulses having energies suitable to cause evoked responses of only the first chamber and result in intrinsic contractions of the second chamber; and wherein the determining means include means for determining the interchamber conduction delays as the times between deliverances of the simultaneous multi-chamber pacing pulses and resulting intrinsic contractions of the second chamber of the heart.

32. The system of claim 31 wherein the corresponding chambers are the ventricles of the heart.

33. The system of claim 31 wherein the corresponding chambers are the atria of the heart.

34. The system of claim 28 wherein the corresponding chambers are the ventricles of the heart.

35. The system of claim 28 wherein the corresponding chambers are the atria of the heart.

36. The system of claim 19 wherein the implantable cardiac device includes pacing means for delivering pacing pulses to the heart; wherein programmed pacing parameters determine the pacing pulses; and wherein the system further includes means for revising the pacing parameters in response to the relative changes in the determined interchamber conduction delays.

37. In an implantable cardiac stimulation device, a method of monitoring progression or regression of a patient's heart disease, the method comprising the steps of:

generating an electrogram of the patient's heart;

processing the electrogram signal to identify cardiac events in the heart activity signal;

deriving from the cardiac event identifications of interchamber conduction delays of the patient's heart by monitoring the progression or regression of the heart disease by determining relative changes in the interchamber conduction delays over time; and storing the interchamber conduction delays in a memory for later review.

38. The method of claim 37 further including the step of conveying the stored interchamber conduction delays from the memory to an external receiver.

39. The method of claim 37 wherein the interchamber conduction delays are the times between activations of ventricles of the patient's heart and wherein the deriving step includes determining the times between activations of the ventricles.

40. The method of claim 37 wherein the interchamber conduction delays are the times between activations of atria of the patient's heart and wherein the deriving step includes determining the times between activations of the atria.

41. The method of claim 37 further including the step of delivering pacing pulses to a chamber of the heart, wherein the deriving step determines the interchamber conduction delays as the times between deliverances of pacing pulses to the chamber of the heart and resulting intrinsic contractions of a corresponding chamber of the heart; and wherein the chamber and the corresponding chamber are the right ventricle and the left ventricle.

42. The method of claim 37 further including the step of delivering pacing pulses to a chamber of the heart, wherein the deriving step determines the interchamber conduction delays as the times between deliverances of pacing pulses to the chamber of the heart and resulting intrinsic contractions of a corresponding chamber of the heart; and wherein the chamber and the corresponding chamber are the right atrium and the left atrium.

43. The method of claim 37 further including the step of delivering pacing pulses to a chamber of the heart; wherein the deriving step determines the interchamber conduction delays as the times between evoked responses of the chamber and the resulting intrinsic contractions of the corresponding chamber; and wherein the chamber and the corresponding chamber are the right ventricle and the left ventricle.

44. The method of claim 37 further including the step of delivering pacing pulses to a chamber of the heart; wherein the deriving step determines the interchamber conduction delays as the times between evoked responses of the chamber and the resulting intrinsic contractions of the corresponding chamber; and wherein the chamber and the corresponding chamber are the right atrium and the left atrium.

45. The method of claim 37 further including the step of delivering simultaneous multi-chamber pacing pulses to corresponding first and second chambers of the patient's heart, the multi-chamber pacing pulses having energies suitable to cause evoked responses of only the first chamber and result in intrinsic contractions of the second chamber, wherein the deriving step determines the interchamber conduction delays as the times between deliverances of the simultaneous multi-chamber pacing pulses and resulting intrinsic contractions of the second chamber of the heart; and wherein the corresponding chambers are the ventricles of the heart.

46. The method of claim 37 further including the step of delivering simultaneous multi-chamber pacing pulses to corresponding first and second chambers of the patient's heart, the multi-chamber pacing pulses having energies suitable to cause evoked responses of only the first chamber and result in intrinsic contractions of the second chamber, wherein the deriving step determines the interchamber conduction delays as the times between deliverances of the simultaneous multi-chamber pacing pulses and resulting intrinsic contractions of the second chamber of the heart; and wherein the corresponding chambers are the atria of the heart.

47. The method of claim 37 further including the step of delivering simultaneous multi-chamber pacing pulses to corresponding first and second chambers of the patient's heart, the multi-chamber pacing pulses having energies suitable to cause evoked responses of only the first chamber and result in intrinsic contractions of the second chamber, wherein the interchamber conduction delays are and the deriving step determines the times between evoked responses of the first chamber and resulting intrinsic contractions of the second chamber of the heart; and wherein the corresponding chambers are the ventricles of the heart.

48. The method of claim 37 further including the step of delivering simultaneous multi-chamber pacing pulses to corresponding first and second chambers of the patient's heart, the multi-chamber pacing pulses having energies suitable to cause evoked responses of only the first chamber and result in intrinsic contractions of the second chamber, wherein the interchamber conduction delays are and the deriving step determines the times between evoked responses of the first chamber and resulting intrinsic contractions of the second chamber of the heart; and wherein the corresponding chambers are the atria of the heart.

49. The method of claim 37 wherein the implantable cardiac stimulation device applies pacing pulses to the heart in accordance with programmed pacing parameters; and wherein the method further includes the step of revising the pacing parameters in response to the relative changes in the derived interchamber conduction delays.

50. In an implantable cardiac stimulation device, a system that monitors progression or regression of a patient's heart disease, the system comprising:

a pulse generator that provides simultaneous multi-chamber pacing pulses corresponding first and second chambers of the patient's heart, the multi-chamber pacing pulses having energies suitable to cause evoked responses of the first chamber and result in intrinsic contractions of the second chamber;

a detector that detects the intrinsic contractions;

a processor, coupled to the detector, that determines interchamber conduction delays between the corresponding chambers, wherein the processor monitors the progression or regression of the patients heart disease by determining relative changes in the interchamber conduction delays over time; and a memory that stores the interchamber conduction delays for later analysis.

51. The system of claim 50 wherein the pulse generator output further delivers pacing pulses to the heart; wherein programmed pacing parameters determine the pacing pulses; and wherein the processor is configured to revise the pacing parameters in response to the relative changes in the determined interchamber conduction delays.

52. The system of claim 50 wherein the processor is configured to determine the interchamber conduction delays as the times between provision of the simultaneous multi-chamber pacing pulses and resulting intrinsic contractions of the second chamber of the heart.

53. The system of claim 52 wherein the corresponding chambers are the ventricles of the heart.

54. The system of claim 52 wherein the corresponding chambers are the atria of the heart.

55. The system of claim 50 wherein the processor is configured to determine the interchamber delays as the times between evoked responses of the first chamber and resulting intrinsic contractions of the second chamber of the heart.

56. The system of claim 55 wherein the corresponding chambers are the ventricles of the heart.

57. The system of claim 55 wherein the corresponding chambers are the atria of the heart.

* * * * *